United States Patent [19]

Hayakawa et al.

[11] Patent Number: 5,232,498

[45] Date of Patent: Aug. 3, 1993

[54] APPARATUS FOR APPLYING GEL TO AN ULTRASONIC PROBE

[75] Inventors: Kenichi Hayakawa, Kawasaki; Takaki Shimura, Machida; Kenji Kawabe, Yokohama, all of Japan

[73] Assignee: Fujitsu Limited, Kawasaki, Japan

[21] Appl. No.: 621,208

[22] Filed: Dec. 3, 1990

[30] Foreign Application Priority Data

Dec. 4, 1989 [JP] Japan ................... 1-313445
Dec. 6, 1989 [JP] Japan ................... 1-315411

[51] Int. Cl.⁵ ............................ B05C 1/00; B05C 1/14; B05C 1/08
[52] U.S. Cl. ..................................... 118/203; 118/244; 118/257; 118/258
[58] Field of Search ............... 118/244, 257, 258, 261, 118/680, 203

[56] References Cited

U.S. PATENT DOCUMENTS

| | | | |
|---|---|---|---|
| 146,383 | 1/1874 | Coutant | 118/257 |
| 305,895 | 9/1884 | Conwell | 118/261 |
| 506,184 | 10/1893 | McDonald | 118/257 |
| 632,059 | 8/1899 | McCreery | 118/244 X |
| 1,147,161 | 7/1915 | Goldsmith | 118/244 X |
| 2,445,253 | 7/1948 | Verhoek et al. | 118/257 X |
| 2,952,239 | 9/1960 | Stover | 118/244 |
| 3,335,046 | 8/1967 | Current et al. | 118/257 X |
| 3,681,121 | 8/1972 | Rizzo | 118/257 X |
| 3,718,115 | 2/1973 | Lee | 118/203 |
| 4,006,052 | 2/1977 | Wang | 118/257 X |
| 4,014,287 | 3/1977 | Green | 118/261 X |
| 4,310,576 | 1/1982 | Hesselmann et al. | 118/244 X |
| 4,455,845 | 6/1984 | Schiffer | 118/257 X |

FOREIGN PATENT DOCUMENTS

905991 9/1962 United Kingdom .............. 118/244

Primary Examiner—W. Gary Jones
Assistant Examiner—Steven P. Griffin
Attorney, Agent, or Firm—Nikaido, Marmelstein, Murray & Oram

[57] ABSTRACT

The applicator according to the present invention applies an ultrasonic gel to an ultrasonic wave radiating surface of a probe. The applicator includes a container containing the ultrasonic gel, a belt partly immersed in the ultrasonic gel in the container and partly protruding therefrom and exposed to the outside, and a belt drive unit driven by rollers for drawing up the ultrasonic gel in the container to an exposed position outside of the container.

16 Claims, 7 Drawing Sheets

APPARATUS FOR APPLYING GEL TO AN ULTRASONIC PROBE

BACKGROUND OF THE INVENTION

1. Field of the Invention

The present invention relates to an ultrasonic diagnostic apparatus, and particularly to an applicator of a gel or jellied material (hereinafter referred to as ultrasonic gel) for applying the ultrasonic gel to an ultrasonic wave radiating surface of a probe, to ensure a close fit of the probe to a patient's body and enable an easy penetration of the body an ultrasonic wave.

2. Description of the Related Art

The ultrasonic gel is applied to the ultrasonic wave radiating surface of the probe to ensure a close fit of the ultrasonic wave radiating surface to the patient's body and an efficient penetration of the body by the ultrasonic wave. To ensure this close fit, the ultrasonic gel must be entirely and uniformly applied over the ultrasonic wave radiating surface.

Figure 11:
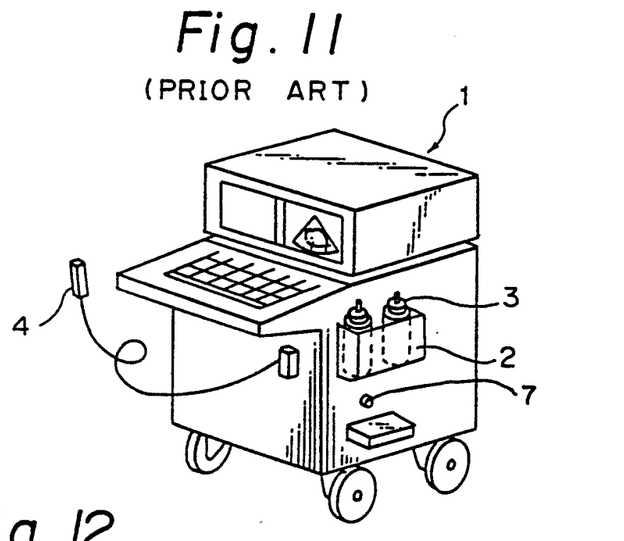
FIG. 11 is a perspective view of an ultrasonic diagnostic apparatus according to a prior art.
Figure 12:
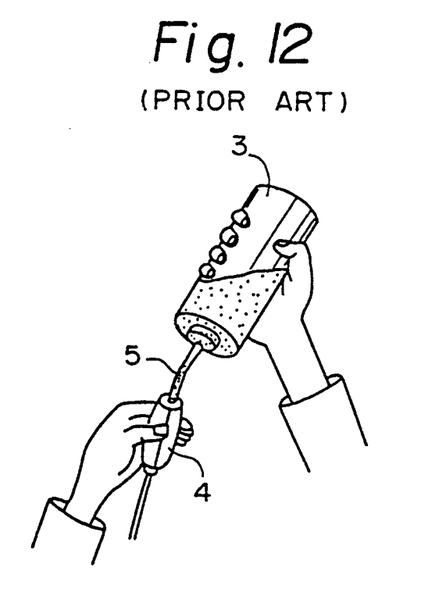
FIG. 12 shows a conventional method of applying an ultrasonic gel to an ultrasonic wave radiating surface of a probe.
Figure 13:
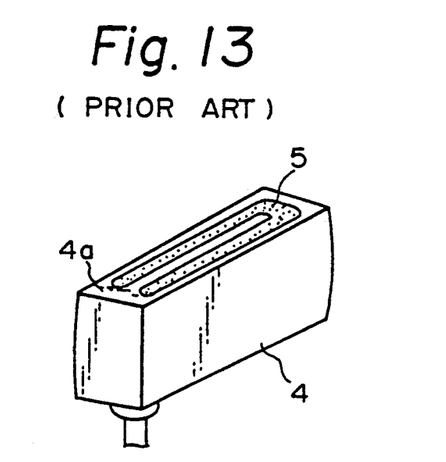
FIG. 13 is a view showing the ultrasonic wave radiating surface of the probe to which the ultrasonic gel has been applied by the conventional method.

FIG. 11 is a perspective view showing an ultrasonic diagnostic apparatus according to a prior art, FIG. 12 shows a conventional method of applying the ultrasonic gel to an ultrasonic wave radiating surface of a probe, and FIG. 13 shows the ultrasonic wave radiating surface of the probe with the ultrasonic gel applied thereto by the conventional method. In FIG. 11, the ultrasonic diagnostic apparatus 1 is provided with a box 2 on a side frame of the apparatus. This box 2 accommodates containers 3 for containing the ultrasonic gel. When using a probe 4, an operator holds the probe 4 with one hand, with an ultrasonic wave radiating surface 4a of the probe 4 facing upward, and the container 3 with the other hand as shown in FIG. 12. The operator then exerts a strong gripping force onto the container 3, to squeeze the ultrasonic gel 5 out of the container 3, and applies the ultrasonic gels to the ultrasonic wave radiating surface 4a of the probe 4 as shown in FIG. 13.

As explained above, both hands must be used when applying the ultrasonic gel to the probe 4, and further, since presently marketed ultrasonic gel is highly viscous, the container 3 must be swung before squeezing the ultrasonic gel 5 there from when only a small amount of the ultrasonic gel 5 remains in the container 3.

Also, an excessive quantity of the ultrasonic gel 5 may be squeezed from the container 3, which is wasteful of the gel 5, or a too small quantity of the gel 5 energes and thus must be repeatedly applied to the probe after the probe is applied to a patient's body.

As shown in FIG. 12, it is difficult to uniformly apply the ultrasonic gel 5 to the ultrasonic wave radiating surface 4a of the probe 4 while squeezing the container 3 with one hand, and as a result, air exists between the ultrasonic wave radiating surface 4a and the patient's body when the probe 4 is applied there to, and the existing air finderes the radiation of the ultrasonic waves.

SUMMARY OF THE INVENTION

To solve these problems, an object of the present invention is to provide an applicator for quickly and simply applying a proper quantity of ultrasonic gel to an ultrasonic wave radiating surface of a probe.

To achieve the above object, an applicator according to the present invention is provided for applying an ultrasonic gel to an ultrasonic wave radiating surface of a probe. The applicator comprises a container containing the ultrasonic gel, a belt partly immersed in the ultrasonic gel in the container and partly protruding and exposed at the top of the container, and a belt drive means having rollers for driving the belt to draw up the ultrasonic gel in the container to the exposed position at the top of the container.

The rollers drive the belt in one direction, and the belt transports the ultrasonic gel in the container into the air. The ultrasonic wave radiating surface of the probe is pushed down on to the exposed upper face of the belt on which the ultrasonic gel is entrained, so that the ultrasonic gel is thus applied to the surface of the prode. To consecutively apply the ultrasonic gel to the surface, the rollers are further rotated to thereby pull up more ultrasonic gel, and the gel is applied to the probe in the same manner.

Another aspect of the present invention provides an apparatus for applying the ultrasonic gel to an ultrasonic wave apparatus for applying the ultrasonic gel to an ultrasonic wave radiating surface of a probe. The apparatus comprises a container containing the ultrasonic gel, a roller partly immersed in the ultrasonic gel and partly protruding and exposed at the top of the container, and a means (rotary shaft) for rotatably supporting the roller.

The roller rotates around the rotary shaft and entrains the ultrasonic gel stored in the container and moves the gel into the air. At this time, the probe is also moved, such that the ultrasonic gel on the exposed surface of the roller is applied to the ultrasonic wave radiating surface of the probe. To continuously apply the ultrasonic gel to the probe, the ultrasonic wave radiating surface of the probe may be pressed against the exposed periphery of the roller and moved in such a manner that the roller is rotated and continnuously draws up the ultrasonic gel.

DESCRIPTION OF THE PREFERRED EMBODIMENTS

Figure 1A:
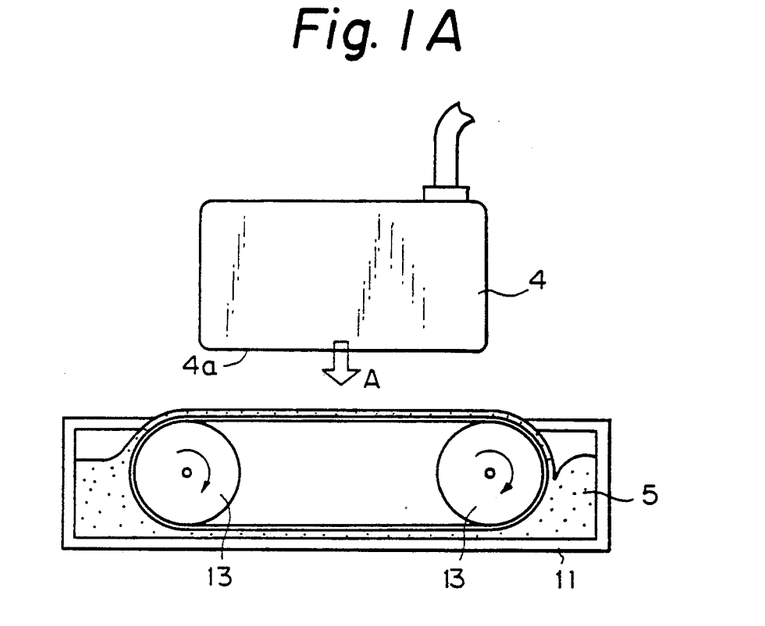
FIG. 1A is a front view showing the principle of an ultrasonic gel applicator according to the present invention.
Figure 1B:
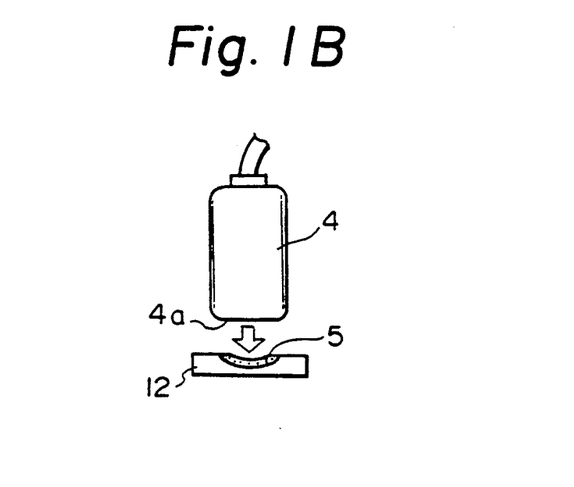
FIG. 1B is a side view showing the applicator of FIG. 1A.

The applicator according to the present invention shown in FIGS. 1A and 1B, applies an ultrasonic gel 5 to an ultrasonic wave radiating surface 4a of a probe 4. In general, the ultrasonic gel 5 is preferably composed of, for example, a polymer, a humidity-maintenance agent, a surface-active agent, distilled water, and a coloring agent and retention material for food, and so on.

The applicator comprises a container 11 containing the ultrasonic gel 5, a belt 12 partly immerssed in the ultrasonic gel 5 in the container 11 and partly protruding and exposed at top of the container 11, and a belt drive means having rollers 13 for driving the belt 12 to thereby draw up the ultrasonic gel 5 in the container 11 to the exposed position at the top of the container 11.

In FIG. 1A and 1B, the rollers 13 drive the belt 12 in one direction, and the belt 12 transports the ultrasonic gel 5 in the container 11 to exposed position at the top of the container 11. The ultrasonic wave radiating surface 4a of the probe 4 is pushed down on to the upper face of the belt 12, on which gel 5 is entrained, in the direction of an arrow A, so that the ultrasonic gel 5 is thus applied to the radiating surface 4a of the prode 4.

To consecutively apply the ultrasonic gel 5 to the rodiating surface 4a, the rollers 13 are further rotated to pull up fresh ultrasonic gel 5 and apply same to the probe 4 in the same manner.

The belt 12 driven by the rollers 13 is an endless belt, as shown in the drawings, and the lower side of the belt 12 is immersed in the ultrasonic gel 5 in the container 11, and the upper side thereof is exposed at the top of the container 11. The upper side of the belt 12 forms a horizontal flat area having a length at least longer than the length of the ultrasonic wave radiating surface 4a of the probe 4. As shown in FIG. 1B, the ultrasonic wave radiating surface 4a of the probe 4 usually is provided with an acoustic lens having a convex cross section. To apply the ultrasonic gel 5 to the convex surface and to form a gel applying gap between the roller 13 and the probe 4 pushed against the roller 13, a recess may be formed in the roller 13 to be in contact with the probe 4, or the contact face of the belt 12 may be made of a porous material such as sponge.

Figure 2:
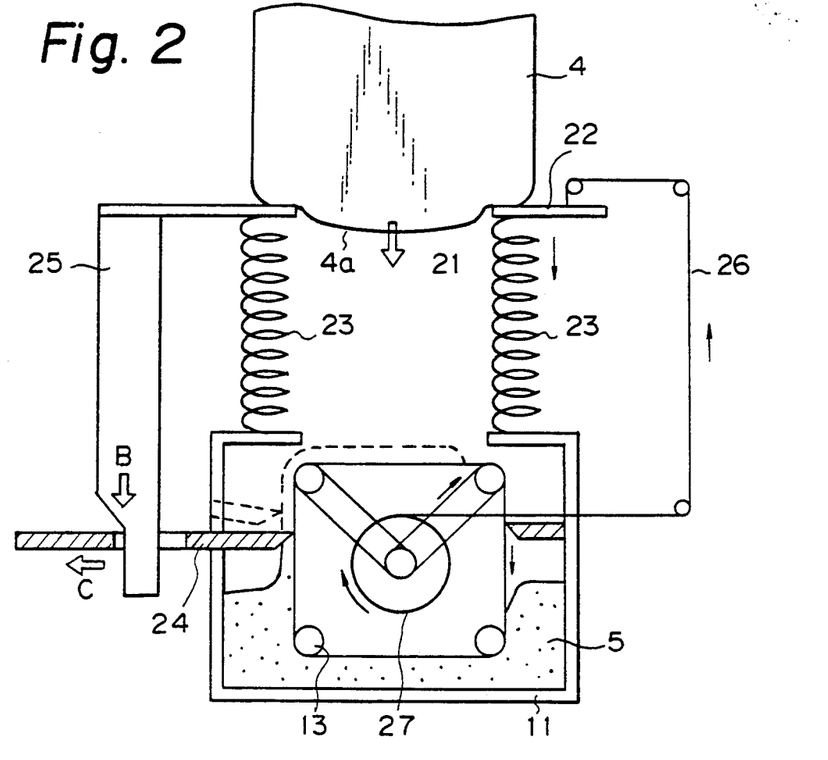
FIGS. 2 to 4 are views showing ultrasonic gel applicators according to embodiments of the present invention.
Figure 3:
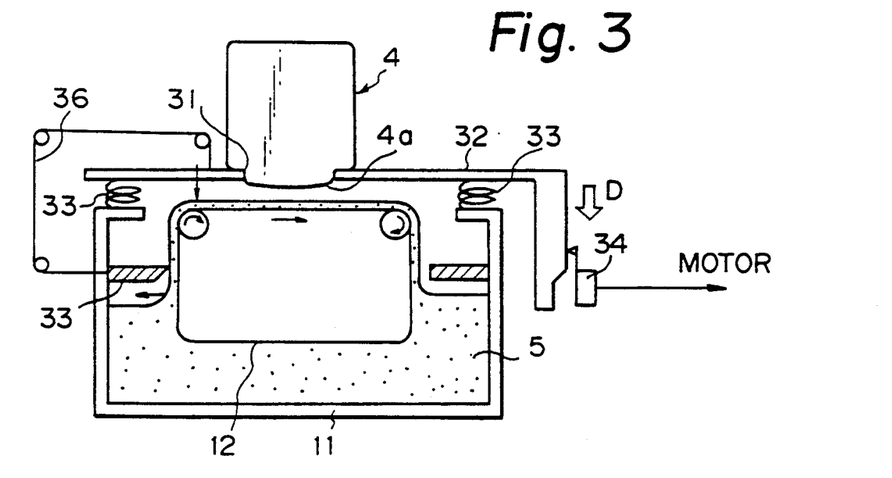
Figure 4:
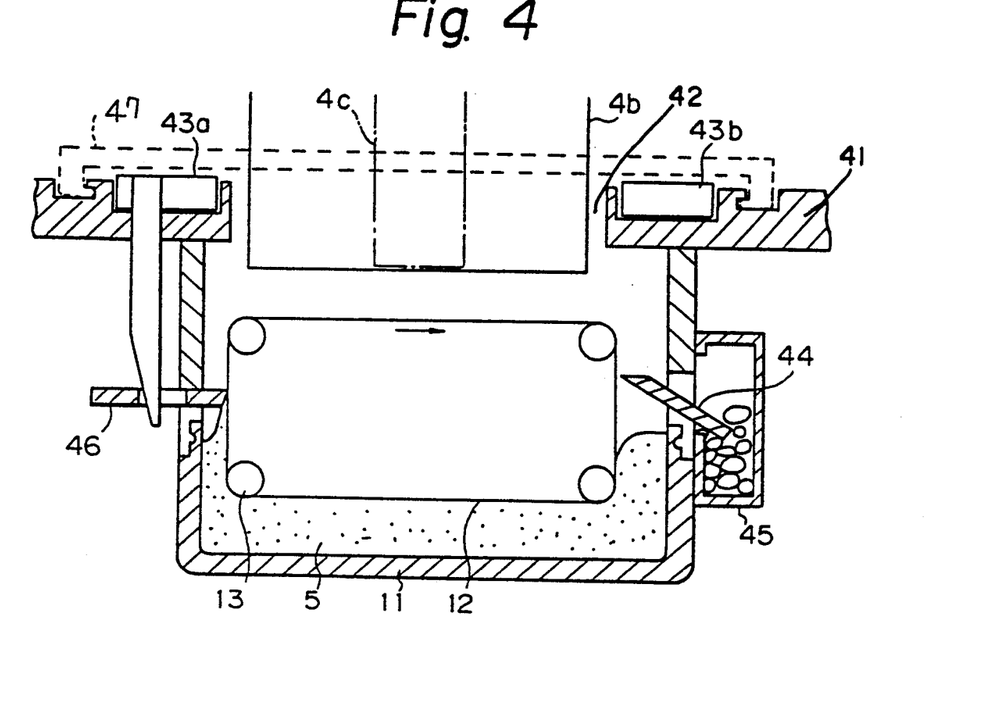

FIGS. 2 to 4 show ultrasonic gel applicators according to other embodiments of the present invention. In FIG. 2, a plate (touch plate) 22 has a hole 21 through which passes an ultrasonic wave radiating surface 4a of a probe 4. The touch plate 22 is disposed on a gel container 11 above a belt 12 and supported by a spring 23. When the touch plate 22 is pushed down toward the belt 12, a pulley 27 is driven through a wire 26, to thereby drive the belt 12. Namely, when the probe 4 is placed on the touch plate 21 and pushed down against the spring 23, ultrasonic gel 5 contained in the container 11 is transported outside of the container 11 and applied to the ultrasonic wave radiating surface 4a of the probe 4.

To prevent an unnecessary pick up and drying of the ultrasonic gel 5 in the container 11, a blade 24 is arranged on the upstream side of the direction of rotation of the belt 12, and the blade 24 is usually pushed against the belt 12 by a spring (not shown). Therefore, when the belt rotates and carries surplus gel 5, the blade 24 presses against and scrapes the ultrasonic gel 5 from the belt 12 into the container 11. When the probe 4 is placed on the touch plate 21, to push down the touch plate 21, a blade opening/closing member 25 descends in the direction of an arrow mark B and opens the blade 24 in the direction of an arrow mark C, to thereby allow the ultrasonic gel 5 to be picked up and transported to the probe 4.

According to the embodiment of FIG. 3, a plate (touch plate) 32 is provided with a hole 31 through which passes an ultrasonic wave radiating surface 4a of a probe 4, similar to the embodiment of FIG. 2. The touch plate 32 is disposed on a gel container 11 above a belt 12 and supported by a spring 33. When the touch plate 32 is pushed down toward the belt 12 in the direction of an arrow mark D, a limit switch 34 is activated to start a motor (not shown) that drives the belt 12. The thus-driven belt 12 entrains the ultrasonic gel 5, and when the belt 12 has rotated by about a half turn, another limit switch (not shown) stops the motor. After the ultrasonic gel 5 in the container 11 is transported outside thereof and the belt 12 is stopped, the ultrasonic wave radiating surface 4a of the probe 4 is pressed against the belt 12, and the ultrasonic gel 5 is applied to the surface 4a. Similar to the embodiment of FIG. 2, the embodiment of FIG. 3 has a blade 35 for scraping the surplus ultrasonic gel 5 from the belt 12. In this embodiment, a wire 36 interlocking with the touch plate 32 drives the blade 35.

According to the embodiment of FIG. 4, photosensors 43a and 43b are disposed at an entrance 42 of a surface plate 41. When a probe 4 comes inside the surface plate 41, a motor (not shown) for driving a belt 12 is activated so that the belt 12 entrains the ultrasonic gel 5 and transports it outside. Similar to the embodiment of FIG. 3, a limit switch (not shown) is arranged to stop the belt 12 after it has rotated for a half turn, and an ultrasonic wave radiating surface of the probe 4 (a linear probe 4b or a sector probe 4c) is pressed against the ultrasonic gel 5 on the belt 12 to apply the gel 5 to the radiating surface. To remove surplus ultrasonic gels exposed to the air and dried from the belt 12, a cleaning lever 44 is disposed on the downstream side of the direction of rotation of the belt 12. The cleaning lever 44 is pushed against the belt 12 by an appropriate spring (not shown), so that the cleaning lever 44 is in contact with the belt 12 to scrape the ultrasonic gel from the belt 12 and a waste box 45. The waste box 45 may be a disposable unit and may be attached to the container 11. On the upstream side of the direction of rotation of the belt 12, a thickness adjusting member 46 movable toward and away from the belt 12 is provided, to adjust the thickness of ultrasonic gel 5 transported by the belt 12. When this apparatus is not in use, the member 46 is pushed against the belt 12 by an appropriate spring (not shown), so that the gap between the belt 12 and the member 46 is completely closed. On the other hand, when the apparatus is in use, the member 46 is moved away from the belt 12, to define an appropriate gap therebetween.

Also when the apparatus is not in use, the gel container 11 may be covered with a cap 47, so that the ingress of foreign substances to the container 11 is prevented. The container 11 may be constructed as a disposable unit formed as an independent unit from the waste box 45, or as an integral unit with the waste box 45.

Figure 5:
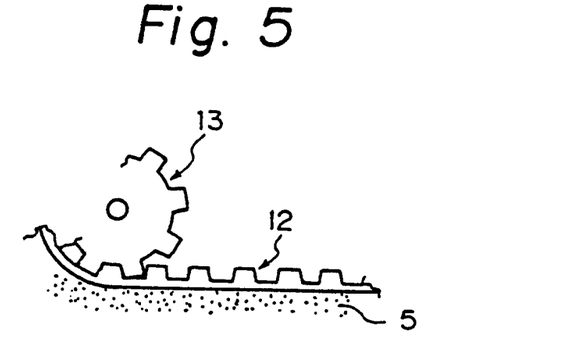
FIG. 5 is a partial detailed view of a roller and belt of FIG. 4.

As shown in FIG. 5, the belt 12 is preferably a toothed belt and the drive roller 13 is provided with a gear which engages with the toothed belt 12, so that a part of ultrasonic gel 5 is prevented from entering the gap between the toothed belt and the gear roller 13, and thus the belt 12 can be always stably driven by the gear roller 13.

As explained above, according to the above embodiment, the rollers 13 are rotated to drive the belt 12, to thereby draw up the ultrasonic gel 5 in the container 11 to the exposed position. The gel is uniformly distributed over the belt 12, and the operator holds the probe 4 with one hand and presses the ultrasonic wave radiating surface 4a against the upper face of the belt 12. Accordingly, by this simple operation, the ultrasonic gel 5 is uniformly applied to the ultrasonic wave radiating surface 4a.

Figure 6A:
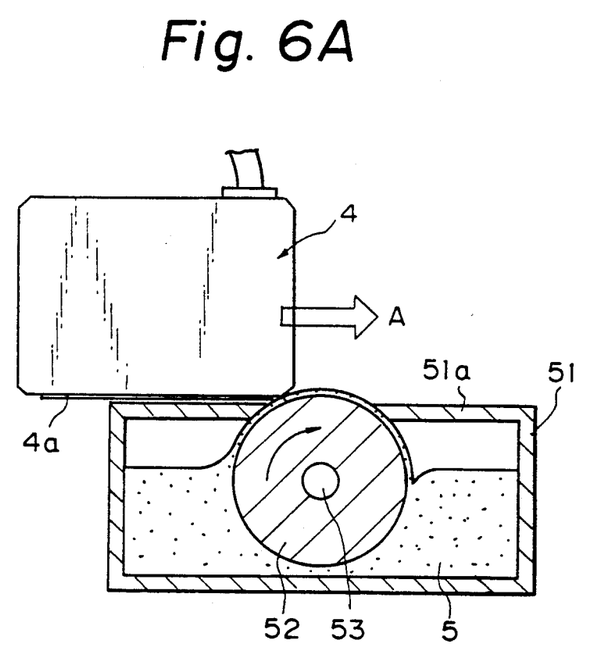
FIG. 6A is a view showing the principle of an ultrasonic gel applicator according to the present invention.
Figure 6B:
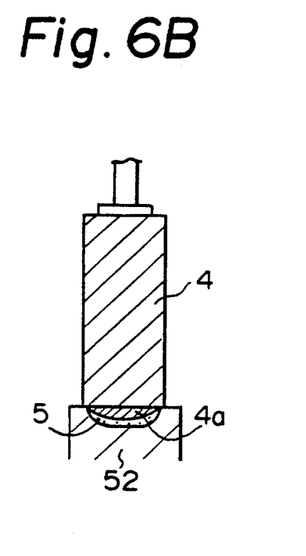
FIG. 6B is a side view showing the applicator.

FIGS. 6A and 6B are front and side views showing another ultrasonic gel applicator of the present invention.

As shown in FIGS. 6A and 6B, the present invention provides an apparatus for applying the ultrasonic gel 5 to an ultrasonic wave radiating surface 4a of a probe 4. The apparatus comprises a container 51 containing the ultrasonic gel, a roller 52 partly immersed in the ultrasonic gel and partly protruding and exposed at the top of the container 51, and a means (rotary shaft) 53 for rotatably supporting the roller.

In FIGS. 6A and 6B, the roller 52 rotates around the rotary shaft 53 and entrains the ultrasonic gel 5 stored in the container 51, and transports the gel 5 to the exposed position. At this time, the probe 4 is moved in the direction of an arrow A, and the ultrasonic gel 5 on the surface of the roller 52 is applied to the ultrasonic wave radiating surface 4a of the probe 4. To continuously apply the ultrasonic gel to the probe 4, the ultrasonic wave radiating surface 4a of the probe 4 may be pressed against the periphery of the roller 52 and moved in the direction of the arrow A, to rotate the roller 52 and draw up the ultrasonic gel 5.

The roller 52 is rotatably supported by the rotary shaft 53 such that the upper part of the roller 52 is exposed at an upper face 51a of the container 51. On the upstream side of the direction of rotation of the roller 52, a gap exists between the roller 52 and the upper face 51a, to ensure that a required thickness of ultrasonic gel is applied to the periphery of the roller 52. The ultrasonic wave radiating surface 4a of the probe 4 is moved in the direction of the arrow mark A on the upper face 51a of the container 51, such that the surface 4a is in contact with the periphery of the roller 52. As shown in FIG. 6A, the ultrasonic wave radiating surface 4a of the probe 4 usually has an acoustic lens having a convex cross section, and to properly apply the ultrasonic gel 5 to the convex surface, a gap must be formed between the convex surface and the roller 52 when the convex surface is pushed against the roller 52. Accordingly, a cross sectional shape of the roller 52 to be in contact with the probe 4 may be recessed, or a contacting surface of the roller 52 may be made of porous a material such as sponge.

Figure 7:
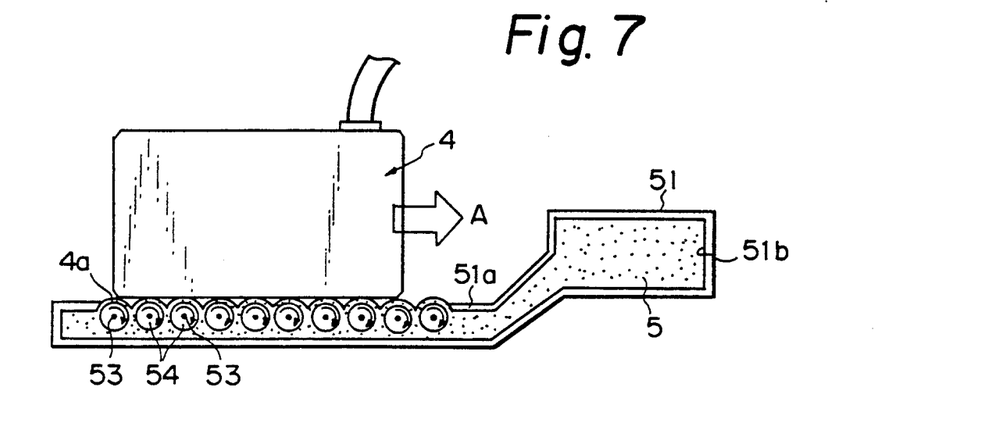
FIG. 7 is a view showing a first embodiment of the present invention.

FIGS. 7 and 8A-C show ultrasonic gel applicators according to further embodiments of the present invention. In FIG. 7, rollers 54 each having a small diameter are horizontally arranged side by side with a small interval therebetween. Each of the rollers 54 is partly immersed in the ultrasonic gel 5. A ultrasonic wave radiating surface 4a of a probe 4 is moved in the direction of an arrow A along an upper face 51a of a container 51 so that the surface 4a is in contact with the peripheries of the rollers 54, and thus the ultrasonic gel 5 attaching to the rollers 54 is applied to the probe 4. This embodiment can apply the ultrasonic gel to the probe 4 while the probe 4 is slightly slid therealong, compared with the case of using a large diameter roller. The container 51 containing the ultrasonic gel 5 is provided with an ultrasonic gel reservoir 51b that continuously supplies the ultrasonic gel 5 to the container 51.

Figures 8A, 8B, 8C:
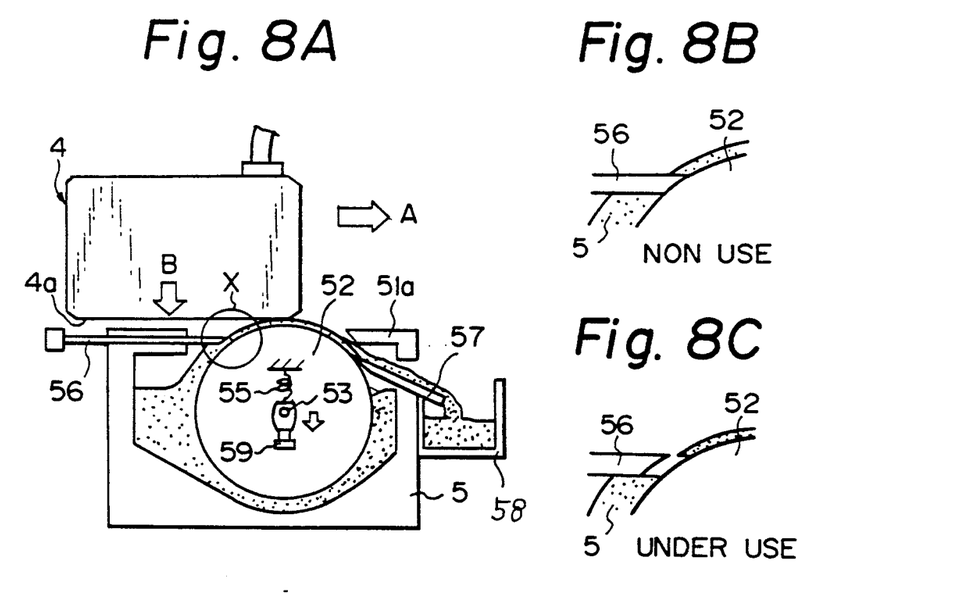
FIG. 8A is a front view showing a second embodiment of the present invention.
FIG. 8B is an enlarged view showing a part X of FIG. 8A with the apparatus being not in use.
FIG. 8C is an enlarged view showing the part X of FIG. 8A, while the apparatus is in use.

In the embodiment of FIGS. 8A-8C, a spring 55 pushes upward a rotary shaft 53 for a roller 52, and when the roller 52 is pushed down against the spring 55, a switch 59 is turned on to drive a motor (not shown) to thereby drive the roller 52. On the upstream side of the direction of rotation of the roller 52 is provided a thickness control lever 56, for controlling the thickness of the ultrasonic gel 5. The lever 56 is adjustable toward and away from the roller 52. On the downstream side of the direction of rotation of the roller 52 is provided a cleaning blade 57 for scraping ultrasonic gels remaining on the surface of the roller 52, and a waste box 58 for receiving the ultrasonic gel 5 scraped off by the cleaning blade 57.

When the applicator is not used, the roller 52 pushed up by the spring 55 is at an upper position as shown in FIG. 8B. At this position, the thickness control lever 56 is in contact with the periphery of the roller 52 so that the ultrasonic gel 5 in the container 51 will not be dried. To apply the ultrasonic gel 5 to an ultrasonic wave radiating surface 4a of a probe 4, the surface 4a is moved in the direction of an arrow mark A along an upper face 51a of the container 51, similar to the previous embodiment. Before applying the ultrasonic gel 5, the probe 4 is pushed downward to move the roller 52 in the direction of an arrow mark B against the spring 55.

When a gap is formed between the thickness control lever 56 and the roller 52 as shown in FIG. 8C, the switch 59 is turned on to drive the motor (not shown). As a result, the roller 52 starts to rotate, and the periphery of the roller 52 entrains the ultrasonic gel 5. Thereafter, the probe 4 is moved in the direction of the arrow mark A. The ultrasonic gel 5 that has not been applied to the probe 4 and remains on the roller 52 is scraped off by the clearing blade 57 and dropped in the waste box 58. Therefore, no ultrasonic gel will remain on the surface of the roller 52, to dry and harden in the air and be mixed with the ultrasonic gel 5 in the container 51.

All of the ultrasonic gel applicators of the above embodiments can be incorporated in an ultrasonic diagnostic apparatus shown in FIG. 11.

As explained above, according to the above embodiment, the motor or the probe 4 turns the roller 52, which entrains the ultrasonic gel stored in the container 51. Accordingly, simply by sliding the probe 4 horizontally along the roller 52, the ultrasonic gel 5 is uniformly applied to the probe 4.

Figure 9:
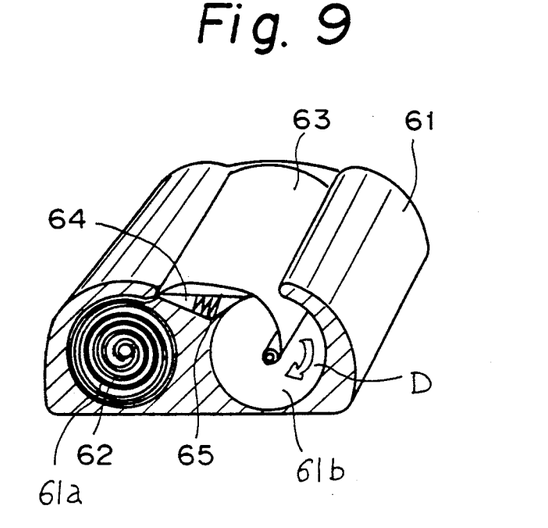
FIGS. 9 and 10 illustrate still another embodiment of this invention.
Figure 10:
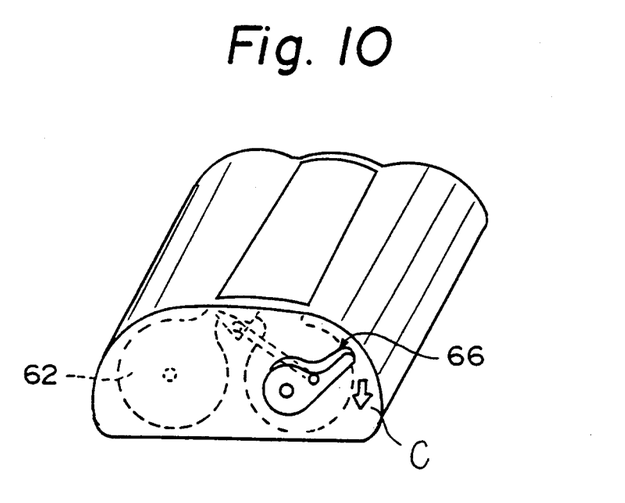

In an embodiment shown in FIGS. 9 and 10, a disposable container 61 has two adjacent chambers 61a and 61b. The first chamber 61a contains a rolled jelly film comprising a flexible base film 62 made of, for example, paper, cloth, rubber or the like, and a jellied or gel material is filled in the first chamber 61a. The rolled film 62 can be drawn to the opened space and wound into the second chamber 61b by a wind-up lever 66, and the first chamber 61a can be closed and opened by a shutter blade 64 provided at the opening of the first chamber 61a.

The shutter blade 64 is corelated with the wind-up lever 66, so that an initial operation of the lever 66 causes the shutter blade 64 to open. During a movement of the lever 66 in the direction of an arrow C, i.e., during a wind-up movement of the film 62 in the direction of an arrow D, the shutter blade 64 is opened, so that the film 62 is wound up and, at the same time, coated with jelly at the open space. At the final stage of the movement of the lever 66 in the direction of an arrow C, the shutter blade 64 is closed by a spring 65, and the lever 66 returns to its initial position. Therefore, when the shutter blade 64 is closed, the jelly in the first chamber 61a is prevented from being exposed to the outside air.

All of the ultrasonic gel applicators of the above embodiments may be incorporated in the ultrasonic diagnostic apparatus as shown in FIG. 11, in that the applicator of the respective embodiments can accommodate the probe of that ultrasonic diagnostic apparatus. Also, for example, a drive power for the applicators can be advantageously obtained from a drive output shaft 7 of the ultrasonic diagnostic apparatus shown in FIG. 11.

We claim:

1. An applicator for applying ultrasonic gel to an ultrasonic wave radiating surface of a probe, said applicator comprising:
a container for containing ultrasonic gel;
a belt having an upper face thereof, said belt being partly immersed in ultrasonic gel in said container and partly protruding therefrom with said upper face exposed outside the container, said belt including a recessed portion for accommodating an uneven surface of said probe;
a belt drive means driven by rollers for drawing up ultrasonic gel in said container to the exposed upper face outside the container, wherein ultrasonic gel is entrained by said upper face of the belt, and an ultrasonic wave radiating surface of a probe is pushed down onto ultrasonic gel entrained by said upper face of the belt;
a waste box disposed along an outer surface of said container;
a cleaning lever at a side of said belt located downstream from the exposed upper face thereof, said cleaning lever being pushed toward said belt by a spring to thereby scrape ultrasonic gel from the belt into the waste box; and
a cover means to prevent ultrasonic gel in the container from being exposed to the air and dried when said applicator is not in use, said cover means engaging said belt, thereby preventing air from entering the container when not in use.

2. An applicator as claimed in claim 1, further comprising a thickness adjusting member at a side of said belt at a position above a surface of ultrasonic gel in said container, said thickness adjusting member being movable toward and away from said belt to thereby adjust the thickness of ultrasonic gel entrained by the belt.

3. An applicator as claimed in claim 1, wherein said waste box is disposable and is detachably attached to said container.

4. An applicator as claimed in claim 3 wherein said gel container is disposable and is detachably attached to said applicator.

5. An applicator as claimed in claim 4, wherein said waste box is constructed integrally with said gel container, so that said gel container with said waste box is disposable and detachably attached to said applicator.

6. An applicator as claimed in claim 1, further comprising a photosensor for detecting an existence of said ultrasonic probe and means for controlling a motor for driving said belt in accordance with a signal from said photosensor.

7. An applicator as claimed in claim 6, wherein at a side of said belt there is a movable element which is movable in such a manner that said photosensor detects a movement of said movable element to detect the existence of said ultrasonic probe.

8. An applicator as claimed in claim 1, wherein said belt comprises a rolled belt, said container comprises a first chamber for containing therein said rolled belt and ultrasonic gel and a second chamber containing therein a windup roller for winding up said belt, one end of said belt is connected to said windup roller so that ultrasonic gel is entrained during a movement of said belt from said first chamber to said second chamber.

9. An applicator as claimed in claim 1, further comprising a member at a side of said belt located upstream from the exposed face thereof and outside of said container, said member being movable toward and away from said belt to thereby shut tightly to make said container airtight and remove ultrasonic gel in the container exposed to the air and dried when said applicator is not in use.

10. An applicator as claimed in claim 9, wherein said member is variably movable toward and away from said belt to adjust the thickness of ultrasonic gel entrained by the belt.

11. An applicator for applying ultrasonic gel as recited in claim 1, wherein said belt includes a toothed inner surface, and at least one of said rollers includes a toothed outer surface which corresponds to said toothed inner surface of said belt.

12. An applicator for applying ultrasonic gel to an ultrasonic wave radiating surface of a probe, said applicator comprising:
a container for containing ultrasonic gel;
a belt having an upper face thereof, said belt being partly immersed in the container and partly protruding therefrom with said upper face exposed outside the container;
a belt drive means driven by rollers for drawing up ultrasonic gel in said container to be exposed outside of the container, wherein ultrasonic gel is entrained by said upper face of the belt, and an ultrasonic wave radiating surface of a probe is pushed down onto ultrasonic gel entrained by said upper surface of the belt;
a cleaning lever at a side of the belt located downstream from the exposed upper face thereof, said cleaning lever being pushed toward said belt by a spring to thereby scrape ultrasonic gel from the belt into a waste box;
a cover means to prevent ultrasonic gel in the container from being exposed to the air and dried when said applicator is not in use; and
a touch plate having a hole through which passes said ultrasonic wave radiating surface of the probe, said touch plate being supported by a spring and being pushed down against a force of the spring toward the belt by the probe, so that said ultrasonic wave radiating surface of the probe comes into contact with said belt.

13. An applicator as claimed in claim 12, wherein said touch plate is correlated with a motor of said belt drive means, so that said motor drives said belt when said touch plate is pushed down against the spring.

14. An applicator as claimed in claim 13, wherein said touch plate is further correlated with a thickness adjusting member provided at a side of said belt and at a position above a surface of ultrasonic gel in said container, so that, when said touch plate is pushed down against the spring, said thickness adjusting member defines a gap between said thickness adjusting member and said belt to thereby adjust a thickness of ultrasonic gel entrained by the belt and, when said touch plate is not pushed down, said thickness adjusting member comes into contact with said belt to prevent ultrasonic gel from being exposed to the air.

15. An applicator for applying ultrasonic gel to an ultrasonic wave radiating surface of a probe, said applicator comprising:
   a container for containing ultrasonic gel;
   a belt having an upper face thereof, said belt being partly immersed in ultrasonic gel in said container and partly protruding therefrom with said upper face exposed outside the container;
   a belt drive means driven by rollers for drawing up ultrasonic gel in said container to the exposed upper face outside of the container, wherein ultrasonic gel is entrained by said upper face of the belt, and an ultrasonic wave radiating surface of a probe is pushed down onto ultrasonic gel entrained by said upper face of the belt;
   a cleaning lever at a side of said belt located downstream from the exposed upper face thereof, said cleaning lever being pushed toward said belt by a spring to thereby scrape ultrasonic gel from the belt into a waste box; and
   a cover means to prevent ultrasonic gel in the container from being exposed to the air and dried when said applicator is not in use;
   wherein said belt comprises a rolled belt, and said container comprises a first chamber for containing therein said roller belt and ultrasonic gel and a second chamber containing therein a windup roller for winding up said belt, one end of said belt being connected to said windup roller such that ultrasonic gel is entrained during a movement of said belt from said first chamber to said second chamber,
   said applicator further comprising a lever for winding up said belt onto said windup roller in said second chamber and a shutter device for opening and closing an outlet of said first chamber in response to an operation of said lever.

16. An applicator for applying ultrasonic gel to an ultrasonic wave radiating surface of a probe, said applicator comprising:
   a container for containing ultrasonic gel;
   a roller partly immersed in ultrasonic gel and partly protruding therefrom and exposed outside the container; and
   a means for rotatably supporting said roller;
   wherein said roller rotates on a rotary shaft, said rotary shaft being springably slidably mounted within said container, such that upon application of pressure to an upper face of said roller, said roller is moved downward, and wherein said apparatus further comprises a switch which is actuated when said pressure is applied to said roller, thereby engaging rotating means to begin rotation of said roller.

* * * * *